United States Patent [19]

Barberet et al.

[11] Patent Number: Plant 6,274

[45] Date of Patent: Sep. 6, 1988

[54] CARNATION PLANT NAMED 'LONTIENO'

[75] Inventors: Nicole Barberet; Yves Ducloux, both of Antibes, France

[73] Assignee: Laboratoire de Physiologie Vegetale de la Londe, La Londe, France

[21] Appl. No.: 889,506

[22] Filed: Jul. 25, 1986

[51] Int. Cl.[4] ..... A01L 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new carnation cultivar particularly distinguished by its medium sized flowers which exhibit an overall light pink color comprising a combination of Dawn Pink and Venetian Pink, the lighter color being at the margins of the petals which are many in number presenting a very pleasing ball form, the blooms being borne on long, strong, upright stems having moderately abundant foliage. The plant blooms profusely during recurrent periods from spring to fall on a tall, upright bush having vigorous growth with good strength.

1 Drawing Sheet

BACKGROUND OF THE NEW PLANT

Our new carnation cultivar is the result of breeding efforts carried on by us at La Londe, Les Maures, France, with the object of producing plants of good quality, nice color and resistance to *Fusarium oxysporum,* this new plant having been selected from a group of seedlings resulting from our crossing of selected and individually identified plants from among our stock of plants maintained at La Londe for breeding purposes. This particular seedling was selected by us for propagation and test because of its very pleasant overall pink color and its substantially solid ball shaped flower form and its propagation was done at La Londe by means of cuttings with very favorable results, which prompted us to direct continued propagation of the new plant through successive generations by cuttings from preceding generations to test its retention of the novel characteristics of the original seedling. It was found that the good and novel characteristics of the parent plant were fully retained from generation to generation and appeared to be firmly fixed.

DESCRIPTION OF THE DRAWING

Our new carnation plant is illustrated by the accompanying photographic drawing which shows, in full color, an arrangement of stems to show the flowers in various stages of opening from newly divided but to maturity, the colors shown being as nearly true to those specified herein as is reasonably possible to obtain by conventional photographic procedures.

DESCRIPTION OF THE NEW PLANT

The following is a detailed description of our new carnation cultivar based upon observations of greenhouse grown plants made at La Londe, France, early in 1983, as well as at Antibes, Alpes-Maritimes, France, the color designations being specified according to The R.H.S. Colour Chart published by The Royal Horticultural Society at London, England.

THE PLANT

Origin: Seedling.

Parentage:

*Seed parent.*—Breeding Variety No. 9 P 13.

*Pollen parent.*—Breeding Variety No. 8391 P. These varieties are growing among our collection of carnation plants maintained at La Londe and are individually recorded in our records of breeding activities.

Classification:

*Botanic.—Dianthus caryophyllus.*

*Commercial.*—Standard Carnation.

Form: Tall, erect bush comprising at least four stems emanated near the ground from the main stem.

Height: In average, about 102 cm., in eight months.

Main stem:

*Length.*—Less than 15 cm. due to being pinched.

Branching character: Branches are few.

Growth habit: Vigorous, upright and rather rigid.

Foliage:

*Quantity.*—Moderately abundant.

*Number of leaves.*—More than 120.

*Leaf size.*—Averaging about 12.7 cm. long and 1 cm. wide, at the seventh node.

*Leaf shape.*—Lanceolate with acuminate apex and rolled margins.

*Texture.*—Leathery.

*Color.*—Upper side — 189A. Under side — 189A.

*Ribs, veins and rachis.*—Hardly noticeable.

THE BUD

Form: Ovoid.

Size: Medium.

*Diameter.*—Averaging about 1.9 cm.

*Length.*—Averaging about 3 cm.

Opening rate: About normal for carnations.

Color of petals: When sepals first divide and when the petals begin to unfurl, the color is the same as in full bloom.

Sepals: Joined at lower part and having sharp pointed extremity. The sepals are hooded over the bud before dividing and the sepals curl back when the flowers open.

*Color.*—Inside — 145D and 144D near the extremity. Outside — 143C and 144C at the extremity.

Calyx:

*Size.*—Large.

*Shape.*—Funnel-shaped and of medium length.

*Splitting.*—The calyx does not split.

*Aspect.*—Smooth.

Flower stem:
*Length.*—About 74 cm.
*Character.*—Erect and rather rigid.
*Color.*—189A/B.

THE FLOWER

Blooming habit: Recurrent, blooming profusely during the spring, midseason and fall blooming periods with a tendency to give fewer blooms in the fall.
Size of bloom: Medium.
*Diameter.*—Averaging about 8.5 cm.
*Depth.*—About 6 cm.
Borne: Singly.
Shape: High centered when bloom first opens becoming ball shaped with maturity.
Petalage:
*Number of petals.*—About 74 to 84, averaging about 81.
*Arrangement.*—Imbricated.
*Form.*—Fan shaped with rounded edges and being finely serrated at the outer end edges.
*Texture.*—Leathery.
*Appearance.*—Satiny.
*Color.*—Outer petals: Body — Between 49A and 49B. Base — Greenish. Reverse side — 49B. Inside petals: Body — 49A/B. Base — Greenish. Reverse side — 49B.
Petaloids:
*Number.*—About 12 to 24.
*Size.*—Smaller than the petals.
*Color.*—Same as the petals.
Flower stem:
*Length.*—About 74 cm.
*Color.*—189A and B.
Fragrance: Perceptible.

Persistence: The flowers hang on and dry.
Lasting quality:
*As a cut flower.*—At least ten days in vase keeping.
Disease resistance: Resistant to *Fusarium oxysporum* as observed I.N.R.A. Antibes, Alpes-Maritimes, France.

REPRODUCTIVE ORGANS

Stamens:
*Number.*—12 to 22.
*Arrangement.*—Around the ovary.
*Anthers.*—Size: Less than 4 mm. Color: Whitish.
*Filaments.*—Color: Whitish.
Pistils:
*Number.*—2 or 3.
*Styles.*—Color: White.
*Stigmas.*—Color: White and slightly pink.
Character of ovaries: The ovaries are ribbed.

This new carnation variety most nearly resembles 'Barlo' and 'Baruklo'. However, when compared to those varieties, our new plant is lighter in color than 'Baruklo' and darker than 'Barlo', the calyx does not split and the plant is very resistant to *Fusarium oxysporum.*

We claim:

1. A new and distinct carnation variety, substantially as herein shown and described, characterized by the profuse production of medium sized blooms having a generally light pink overall coloration with many petals and of a generally ball shape, the plant being of tall, bush shape with intermittent blooming seasons and profuse production of flowers on long, strong, upright stems.

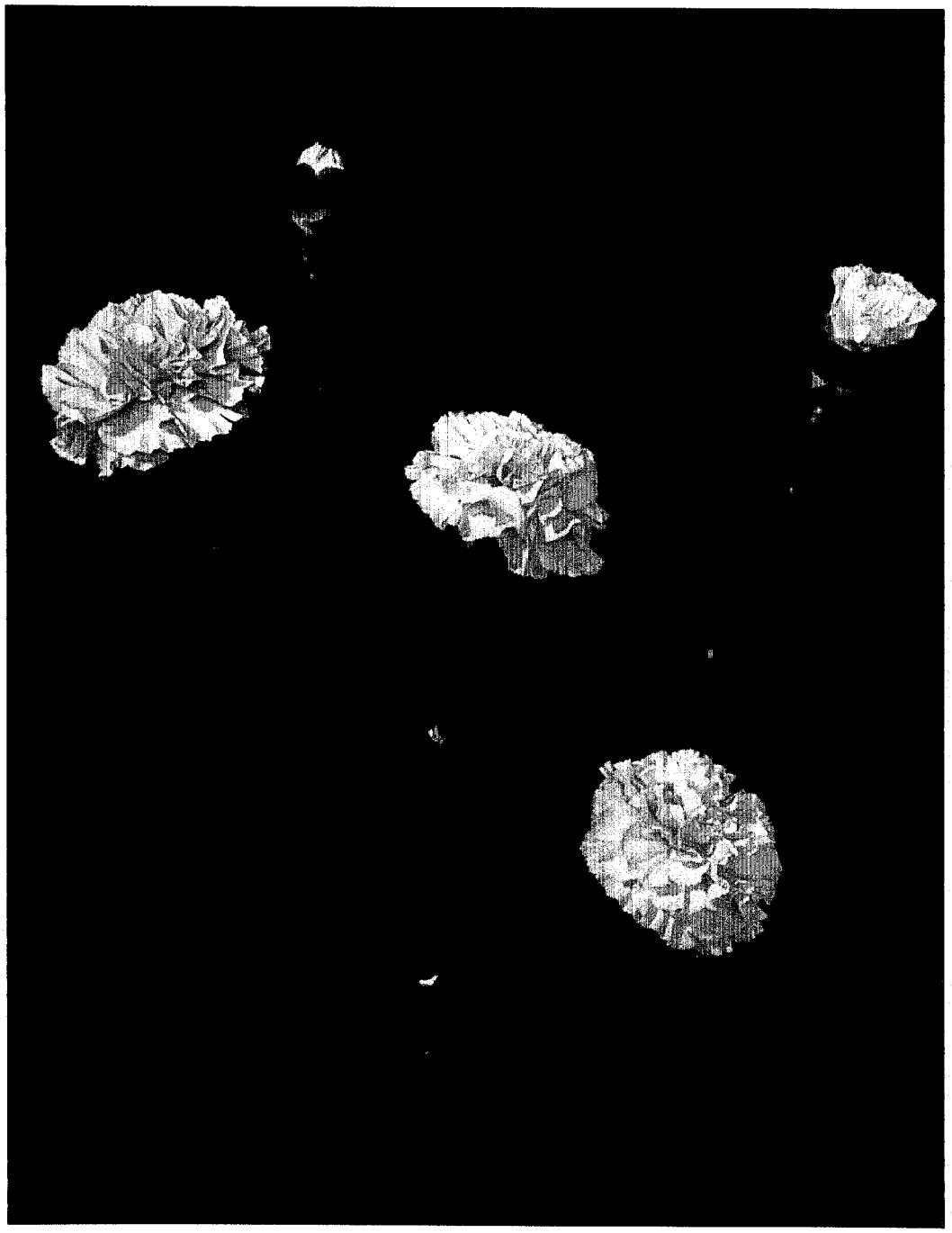

* * * * *